United States Patent [19]

Shapiro

[11] 4,273,869
[45] Jun. 16, 1981

[54] CYSTIC FIBROSIS DETECTION METHOD

[75] Inventor: Burton L. Shapiro, St. Paul, Minn.

[73] Assignee: The Regents of the University of Minnesota, Minneapolis, Minn.

[21] Appl. No.: 30,179

[22] Filed: Apr. 16, 1979

[51] Int. Cl.³ .............................................. C12Q 1/32
[52] U.S. Cl. .................................... 435/26; 435/810; 424/2
[58] Field of Search .................. 424/2, 7; 435/4, 26, 435/805, 810

[56] References Cited

U.S. PATENT DOCUMENTS

| | | | |
|---|---|---|---|
| 3,867,258 | 2/1975 | Forgione | 435/805 |
| 3,899,298 | 8/1975 | Szczesniak | 435/810 |
| 4,019,961 | 4/1977 | Klose | 435/26 |
| 4,042,462 | 8/1977 | Johnson | 435/26 |

OTHER PUBLICATIONS

Denning, "Cystic Fibrosis: Projections into the Future," Stratton Corp., NY, 141-143, 1976.
Nadler, "The Metabolic Basis of Inherited Disease" McGraw Hill, NY, 1978, pp. 1683-1710.
Feigal, "Mitochondrial Calcium Uptake and Oxygen Consumption in Cystic Fibrosis," Nature, vol. 278, 276-277, Mar. 1979.
Shapiro, "Mitochondrial Nadh Dehydrogenase in Cystic Fibrosis," Proc. Natl. Acad. Sci., USA, vol. 76, No. 6, 2979-2983, Jun. 1979.

Primary Examiner—Ernest G. Therkorn
Attorney, Agent, or Firm—Burd, Bartz & Gutenkauf

[57] ABSTRACT

A method of diagnosing cystic fibrosis, identifying carriers for cystic fibrosis, and non-carriers or "normal" persons. Heretofore, no carrier or prenatal detection procedure for cystic fibrosis existed. The detection method is based on the discovery of the genetic abnormality or biochemical defect in cystic fibrosis, which occurs in mitochondria, minute bodies found in the cytoplasma of most cells which are the principal energy source of the cell and contain the cytochrome enzymes of terminal electron transport. The method comprises an assay carried out on preparations derived from human cells possessing mitochondria. The assay may be a kinetic assay of the enzyme complex of the energy conserving site of the mitochondrial electron transport system of the cells or an assay of mitochondrial activity governed by the enzyme complex. The assay is then evaluated by comparison with standards established as the result of similar assays of cells of other subjects of known condition. The assays provide determination of characteristics which differ in the three types of individuals (normal, carrier and affected) and provide a basis for their distinction.

17 Claims, 5 Drawing Figures

CYSTIC FIBROSIS DETECTION METHOD

BACKGROUND OF THE INVENTION

1. Field of the Invention

This invention is directed to an unequivocal method of diagnosing cystic fibrosis, identifying carriers for cystic fibrosis, and non-carriers or "normal" persons.

Cystic fibrosis (CF) is an inherited disease of the exocrine glands, affecting most characteristically the pancreas, respiratory system, and sweat glands. It is transmitted within families as an autosomal recessive trait, affected individuals possessing a double dose of the mutant gene. Biological parents of subjects with CF each possess a single dose of the mutant gene and by definition are obligatory carriers for the condition. Carriers are, however, clinically normal and their detection prior to the birth of an affected child has been precluded by the absence of detectable effects of the gene in single dose. The disease has a 1:4 chance of occurring in a child of either sex if both parents are carriers. It primarily involves Caucasians and usually begins in infancy.

The disease is typified by chronic respiratory infection, pancreatic insufficiency, and susceptibility to heat prostrations. It is a major cause of death in children. It is estimated that there are between ten and twelve million carriers for cystic fibrosis in the United States. Eacy year between two and three thousand children are born in the United States who are affected by cystic fibrosis. The cost of therapy for cystic fibrosis patients is estimated at between about $15,000 to $20,000 per year per patient. Of patients diagnosed in early childhood, fewer than fifty percent reach adulthood.

2. The Prior Art

Prior to this invention, no carrier or prenatal detection procedure for cystic fibrosis existed. (Denning, C. R., et al: "Cystic Fibrosis: Projections into the Future", Mangos, J. A., Editors, Stratton Corporation, New York, pages 141-143, 1976) Diagnosis of the disease state was based on clinical signs and increased sweat salinity. No specific protein or enzyme assay for cystic fibrosis existed. (Nadler, H. L., et al: "The Metabolic Basis of Inherited Disease", Stanbury, J. B. et al, Editors, McGraw-Hill, New York, pages 1683-1710, 1978).

SUMMARY OF THE INVENTION

The detection method of this invention is based on the discovery of the genetic abnormality or biochemical defect in cystic fibrosis. It has been discovered that increased calcium uptake by mitochondria occurs in patients with cystic fibrosis and obligate heterozygotes (HZ=carriers). Mitochondria are minute bodies or structures found in the cytoplasm of most cells. Mitochondria are the principal energy source of the cell and contain the dehydrogenase and cytochrome enzyme systems of terminal electron transport. The genetic abnormality in cystic fibrosis is expressed in the first energy conserving site of mitochondrial electron transport [nicotinamide adenine dinucleotide dehydrogenase (NADH dehydrogenase), (complex 1, NADH: ubiquinone oxidoreductase, NADH: ferricyanide oxidoreductase) (E.C.1.6.5.3.)]. Kinetic characteristics of this enzyme system differ in the three types of individuals (normal, carrier and affected) and provide a basis for their distinction. Mitochondrial activity governed by the enzyme system, such as calcium and oxygen uptake, also differs and is also distinguishable among the three types of individuals.

Broadly stated, the cystic fibrosis detection method according to the present invention comprises an assay carried out on preparations derived from human fibroblasts, lymphocytes, amniotic cells, or any other cell type possessing mitochrondria. A homogenate is prepared of the cells. An assay is then performed on the sample of mitochondrial activity of the cells. This may be a kinetic assay of the enzyme complex of the energy conserving site of the mitochondrial electron transport system of the cells or an assay of mitochondrial activity governed by the enzyme complex. The assay is then evaluated by comparison with standards established as the result of similar assays of cells of other subjects of known condition.

Examples of kinetic parameters of the enzyme complex of the energy conserving site of the mitochondrial electron transport system of the cells include (1) affinity of the enzyme for its substrate (Km), (2) pH optimum for enzyme activity, (3) temperature optimum for enzyme activity, (4) inhibition ($K_I$) by a number of inhibitors of the enzyme, and (5) differential electrophoretic mobility of the enzyme. Mitochondrial activity governed by the enzyme of the energy conserving site include (1) calcium uptake as indicated by intracellular calcium pool size differences, (2) oxygen consumption, and (3) differential inhibition of oxygen consumption.

BRIEF DESCRIPTION OF THE DRAWINGS

The invention is illustrated in part by the accompanying drawings in which.

DETAILED DESCRIPTION OF THE PREFERRED EMBODIMENTS

Figure 1:
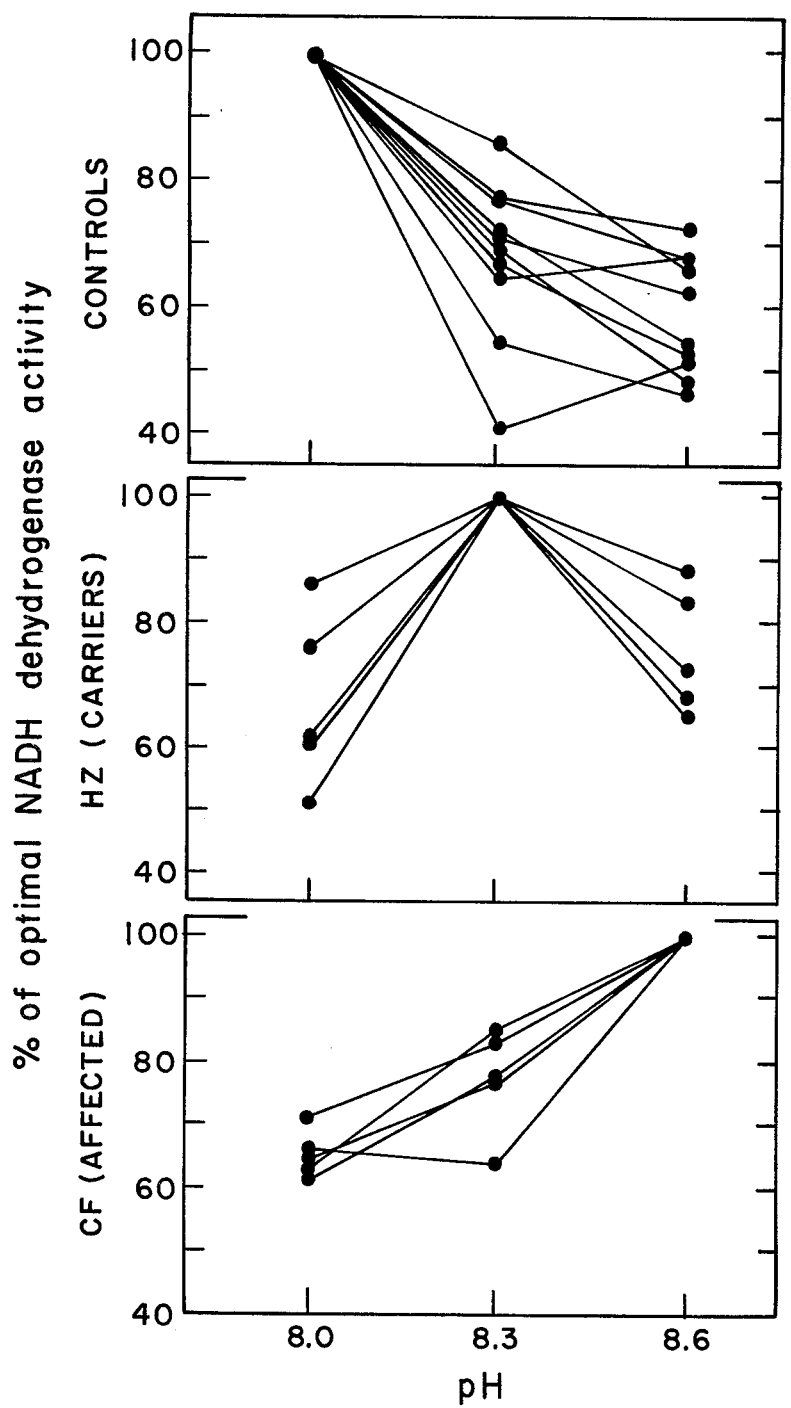
FIG. 1 shows graphically the correlation between pH and optimum enzyme activity in fibroblast cell homogenates from cystic fibrosis patients, carriers, and controls.

The invention is directed to a relatively simple and inexpensive test in the form of a mitochondrial assay for detecting clinically normal carriers for cystic fibrosis and for diagnosing individuals with the disease prior to the onset of symptoms. Heretofore, no method has existed for detection of carriers and affected individuals are diagnosed by physical signs only. No prenatal tests existed. Now carriers for cystic fibrosis can be identified prior to the birth of an affected child. Potential parents of cystic fibrosis children can be counseled as to the risk of having a cystic fibrosis child.

The detection test is based upon the recognition of the fundamental biochemical abnormality in the disease and the application of this knowledge to individual, family and population testing through assay of mitochondrial conditions or activities determined or governed by the enzyme system of the first energy conserving site of the mitochondrial electron transport system of sample cells. The assay tests may be carried out on preparations derived from human fibroblasts, lymphocytes, amniotic cells, or any other cell type possessing mitochondria.

Although cystic fibrosis is considered to be a generalized disease of exocrine glands, skin fibroblasts have been used as a model system for cystic fibrosis studies. Although not exocrine cells, fibroblasts do secrete their products by mechanisms very similar to those which occur in exocrine cells. In addition, the donor's genotype is retained in cultured fibroblasts for many generations. For these reasons, skin fibroblasts were used in the initial studies in connection with the present detection method. It was found that skin fibroblasts from subjects with cystic fibrosis in culture express premature senescence. Increased intracellular calcium ($Ca^{2+}$) which occurs in cells from cystic fibrosis patients and obligate carriers was related to this precocious aging. The site of the altered intracellular calcium pool was traced to mitochondria.

Accumulation of increased calcium by mitochondria is a highly complex and incompletely understood process. One of the systems related to mitochondrial $Ca^{2+}$ influx consists of the terminal steps of oxidation of metabolites since the uphill accumulation of $Ca^{2+}$ in mitochondrial is thought to be driven by a proton gradient generated during electron transport. It was reasoned that the increased sequestration of $Ca^{2+}$ in mitochondria from subjects with cystic fibrosis and carriers might be a reflection of increased electron transport. If this was the case, oxygen consumption would be expected to be increased in these cells. Oxygen consumption in cells was examined from cystic fibrosis patients and age- and sex-matched controls. It was found that cells from cystic fibrosis subjects and obligate carriers do consume significantly more oxygen than do their respective control cells. Following treatment of the cells with the electron transport site 1 inhibitor, rotenone, cells from cystic fibrosis subjects and carriers consume equal amounts of oxygen, as do controls. That is, cells with the different genotypes respond differentially to the inhibitor. Also, mitochondrial NADH dehydrogenase energy conserving site 1 of the electron transport sytem, the target of rotenone, has different properties in cells from cystic fibrosis subjects, carriers and controls. Later studies were based on the use of lymphocytes which are more readily obtained and isolated from venous blood and more readily assayed for enzyme activity.

Assays are carried out using standard methods and procedures well understood in the art.

NADH is the preferred substrate for the kinetic assays of the enzyme but NADPH (nicotinamide adenine dinucleotide phosphate) may be used. Numerous electron acceptors are suitable for determination of enzyme activity including soluble metal ferricyanide salts, the ubiquinones and the tetrazolium salts. Any or all combinations of substrate, buffer constituents and electron acceptors may be used to distinguish the different types of individuals by any or all of the enzyme kinetic characteristics enumerated.

Assay of inhibition of the NADH dehydrogenase may be used to distinguish the three types of individuals, CF affected, carriers and controls. Inhibition is obtained by the use of any of a number of inhibitors of the enzyme including rotenoids, piercidin A, rhein and other quinone analogs, thiol reagents, Demerol, iron chelators, $NAD^+$ (nicotinamide adenine dinucleotide, oxidized form), AMP (adenosine monophosphate), ADP (adenosine diphosphate, ATP (adenosine triphosphate), guanidinium salts, NADH and the general class of barbituates.

For quick, easy identification of CF subjects, carriers, and normal individuals by physicians or hospitals or public health services, the determination of optimum pH for NADH hydrogenase activity is most feasible. The detection system is easily packaged in the form of a kit of three vials, each of which has identical constituents in the form of a liquid mixture including an enzyme substrate and an electron acceptor. Each vial also contains a buffer to establish least alkaline, more alkaline and most alkaline conditions in the respective vials. For example, the vials may be at pH 8.0, 8.3, and 8.6. A suitable sample of cell extract, lymphocytes for example, may then be added to each vial. Depending upon the electron acceptor used, a colormetric, spectrometric or spectrophotofluorometric assay can be used to determine relative enzyme activity. Although the specific activity optima may vary, the relative pH optima among the three groups, CF subjects, carriers and normal individuals, retain the same positions.

The invention is further illustrated by the following examples:

EXAMPLE 1

Preparation of Fibroblast Cell Cultures

Skin fibroblast strains from the upper arm were obtained from subjects with CF and age- and sex-matched controls and from obligate CF heterozygote parents and their age- and sex-matched controls. Cells were stored in liquid nitrogen at early passages and thawed for use as needed. In all but a few experiments, strains were passage matched. For $O_2$ consumption studies and mitochondrial preparations, monolayers were grown in 285×115 mm roller bottles (Bellco Glass, N.J.). For NADH dehydrogenase studies, monolayers were grown in 75 $cm^2$ flasks (Falcon, Oxnard, Ca.). Monolayers were cultured in Eagle's minimal essential medium with Earle's salts plus L-glutamine (K. C. Biologicals, Inc., Lenexa, Kans.), supplemented with 10 percent fetal calf serum, 100 units per ml of penicillin, and 100 µg/ml of streptomycin (Gibco, Grand Island, N.Y.). The cultures were maintained at 37° in 95 percent air-5 percent $CO_2$ atmosphere. Cells were harvested with trypsin-EDTA [(1:250 trypsin+0.2 g EDTA/l (Gibco, Grand Island, N.Y.)].

EXAMPLE 2

Assay of Fibroblast NADH Dehydrogenase Activity

Monolayers of fibroblast cells were grown to confluence. At the time of assay they were rinsed with 3 ml of trypsin-EDTA. Five ml of trypsin-EDTA were added and the monolayer incubated at 37° C. for 10 min. Cells were removed by gentle shaking and transferred to a centrifuge tube containing 1 ml of fetal calf serum (Gibco, Grand Island, N.Y.). An aliquot of 100 µl was removed and suspended in 9.9 ml of Isoton II balanced electrolyte solution (CMS, Minneapolis, Mn.) for cell counting. The cell suspension was centrifuged at 410 g for 5 min, the supernatant discarded and the pellet washed twice with 0.03 M potassium phosphate buffer (pH 7.6) at 0°. The cells were suspended in 2 ml of 0.12 M potassium phosphate buffer (pH 7.6) at 0°. After removal of a 150 µl aliquot for protein analysis the cell suspension was homogenized at 0° at approximately 10,000 rpm in a PT-10 Polytron (Brinkmann, Westbury, N.Y.). The resulting homogenate was centrifuged at 1400×g for 10 min and the supernatant used for assays. Individual flasks yielded between $1.5 \times 10^6$ and $2.5 \times 10^6$ cells, the cell and enzyme activity yields from the three genotypes being equivalent.

Figure 2:
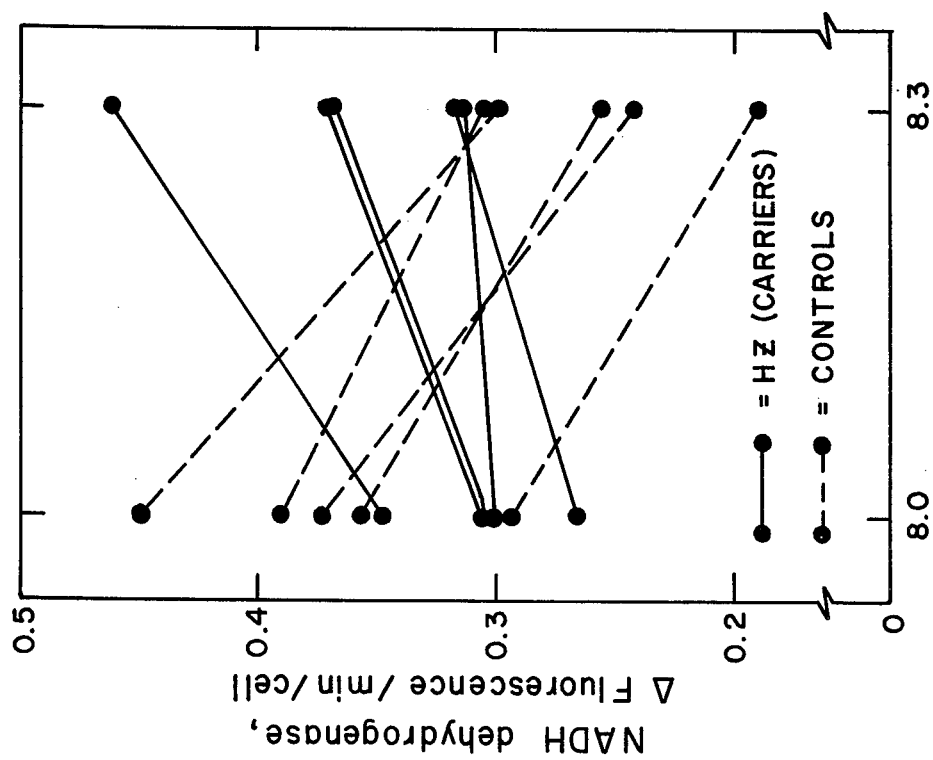
FIG. 2 shows graphically the results of a blind experiment in which cell strains from five controls and five known carriers were assayed for enzyme activity at pH 8.0 and 8.3.

The oxidation of NADH by homogenates was assayed in an Aminco-Bowman spectrophotofluorometer using potassium ferricyanide as an artificial electron acceptor. The excitation and emission wave-lengths for NADH were 350 nm and 470 nm, respectively. The reaction mixture consisted of 200 μl of 0.01 M potassium ferricyanide (Sigma, St. Louis, Mo.), 100 μl of NADH (Sigma) in 0.002 M potassium phosphate buffer, and 2.6 ml of 0.12 M potassium phosphate buffer. NADH concentrations varied between 2.5 and 25 μM. Reaction mixture pH varied between 7.9 and 9.0. Nonenzymatic reaction was recorded first and 100 μl of whole cell extract was added to the reaction mixture to assay the oxidation of NADH. The reaction was assayed at room temperature. Activity of NADH dehydrogenase was expressed as Δ fluorescence (F)/min/mg protein or cell. In some experiments, NADH dehydrogenase obtained from isolated mitochondria was assayed. Determinations of pH optima for NADH dehydrogenase revealed that optimum enzyme activity in cell homogenates occurred at pH 8.6 in CF strains and pH 8.0 in control strains (FIG. 1). The clear and consistent difference in pH optimum for NADH dehydrogenase in CF and control strains occurred at all passages tested (Table 1). We examined pH optima for this enzyme system in strains from obligate heterozygotes and their controls. Optimum pH occurred at pH 8.3 in the carriers and at pH 8.0 in their controls (FIG. 1). The pH optimum of NADH dehydrogenase was recorded on individual cell strains of the three genotypes. Each curve represents a different cell strain.

pH optima were repeatedly different in the three genotypes. In a blind experiment carriers could be distinguished from their controls based on this parameter alone (FIG. 2). Oxidation of NADH by NADH dehydrogenase from whole cell extracts of five control and five heterozygote cell strains was assayed in a blind experiment at pH 8.0 and 8.3. Each line in the graph represents a different cell strain assayed at pH 8.0 and 8.3 Enzyme activity is expressed as Δ fluorescence/min/cell. Without exception enzyme activity was greater at pH 8.3 than at pH 8.0 in carrier strains and at pH 8.0 than at pH 8.3 in controls. Each strain could be diagnosed blindly as to control or CF carrier status by these criteria. Each line represents a different cell strain.

Figure 3:
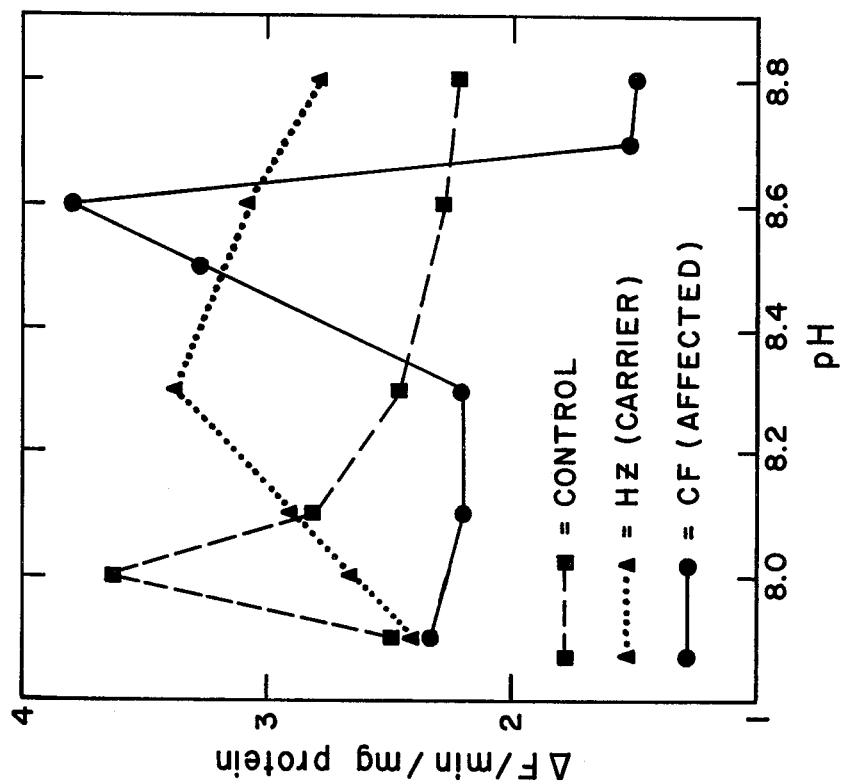
FIG. 3 shows graphically the results of assays at various pH of enzyme activity in isolated mitochondrial preparations from patients, carriers and controls.

The effect of pH on NADH dehydrogenase activity in relatively pure mitochondrial preparations is shown in FIG. 3. A sharp peak occurred at pH 8.0 in the control strains and at pH 8.6 in the CF strain.

TABLE 1

Fibroblast strain source and NADH dehydrogenase kinetics

| Group | Strain | Donor Sex | Age | pH optimum | @ passage(s) | @ pH 8.6 Km (μM) | @ passage | @ pH 8.0 Km (μM) | @ passage |
|---|---|---|---|---|---|---|---|---|---|
| CF | 46 | M | 16 | 8.6 | 5, 6, 10 | 9.8 | 12 | 27.9 | 6 |
| CF | 69 | M | 17 | 8.6 | 4, 10 | 8.5 | 4 | 25.3 | 6 |
| CF | 70 | M | 21 | 8.6 | 4 | 9.8 | 12 | 34.3 | 6 |
| CF | 71 | M | 7 | 8.6 | 4 | 11.7 | 12 | 37.2 | 6 |
| CF | 72 | F | 20 | 8.6 | 10, 11 | 11.4 | 4 | 36.3 | 6 |
| HZ | 73 | F | 54 | 8.3 | 10 | 19.2 | 13 | 18.9 | 14 |
| HZ | 75 | F | 35 | 8.3 | 9, 11 | 20.8 | 13 | 22.7 | 14 |
| HZ | 76 | F | 30 | 8.3 | 9, 11, 12 | 14.5 | 13 | 22.6 | 14 |
| HZ | 77 | M | 60 | 8.3 | 10, 12 | 17.2 | 13 | 19.9 | 14 |
| HZ | 78 | F | 48 | 8.3 | 11, 12 | 19.1 | 13 | 17.9 | 14 |
| C(H) | 81 | F | 32 | 8.0 | 9, 11 | 20.8 | 13 | 22.6 | 14 |
| C(H) | 82 | F | 30 | 8.0 | 10, 12 | 19.2 | 13 | 18.1 | 14 |
| C | 83 | F | 22 | 8.0 | 4, 10, 11 | 17.7 | 12 | 23.2 | 7 |
| C | 84 | M | 20 | 8.0 | 4, 10 | 18.3 | 4 | 21.2 | 7 |
| C | 85 | M | 6 | 8.0 | 5, 10 | 20.2 | 4 | 18.4 | 7 |
| C(H) | 87 | F | 54 | 8.0 | 10 | 16.7 | 13 | 20.7 | 14 |
| C(H) | 88 | F | 43 | 8.0 | 9, 11 | 20.0 | 13 | 18.7 | 14 |
| C(H) | 89 | M | 58 | 8.0 | 10, 11 | 18.2 | 13 | 21.7 | 14 |
| C | 90 | M | 20 | 8.0 | 4 | 17.1 | 12 | 24.2 | 7 |
| C | 91 | M | 20 | 8.0 | 4 | 17.0 | 12 | 25.9 | 7 |

Peak activity in the heterozygote strain was at pH 8.3, but the peak was broad. These experiments were repeated several times with different cell strains with consistent results. Under the conditions used Vmax was equal in the three genotypes.

EXAMPLE 3

Assay of the Affinity of the Enzyme for its Substrate

Apparent affinity of the enzyme NADH dehydrogenase for its substrate (Km) was determined for each cell line at pH 8.0 (the control optimum) and at 8.6 (the CF optimum). No difference in Km between control and HZ strains occurred at either pH. At pH 8.0 Km for the CF strains was significantly greater and at pH 8.6 significantly lower than in the HZ and control strains (Table 1).

EXAMPLE 4

Assay of Lymphocyte NADH Dehydrogenase Activity

Five to 10 cc samples of venous blood are obtained and lymphocytes isolated. Cells are counted, a homogenate is obtained and after centrifugation the relative activity of NADH hydrogenase determined. The substrate is NADH, the electron acceptor in this example is ferricyanide. Enzyme activity is determined at e.g. pH 8.0, 8.3 and 8.6. Change in fluorescence is recorded and expressed as Δ fluorescence/minute/cell. When assayed in this fashion, with or without variations of ingredients or conditions, individuals with the three genotypes can be distinguished unequivocally. NADH activity is always greatest at pH 8.0 in "normal" individuals, at 8.3 in carriers and at 8.6 in subjects with CF. These pH optima may differ depending on reagents and assay conditions. Nevertheless, when various pH's are used it is clear that for CF preparations enzyme activity is greatest at more alkaline conditions, HZ optimum activity at less alkaline conditions and control optimal enzyme activity at relatively the least alkaline conditions.

Figure 4:
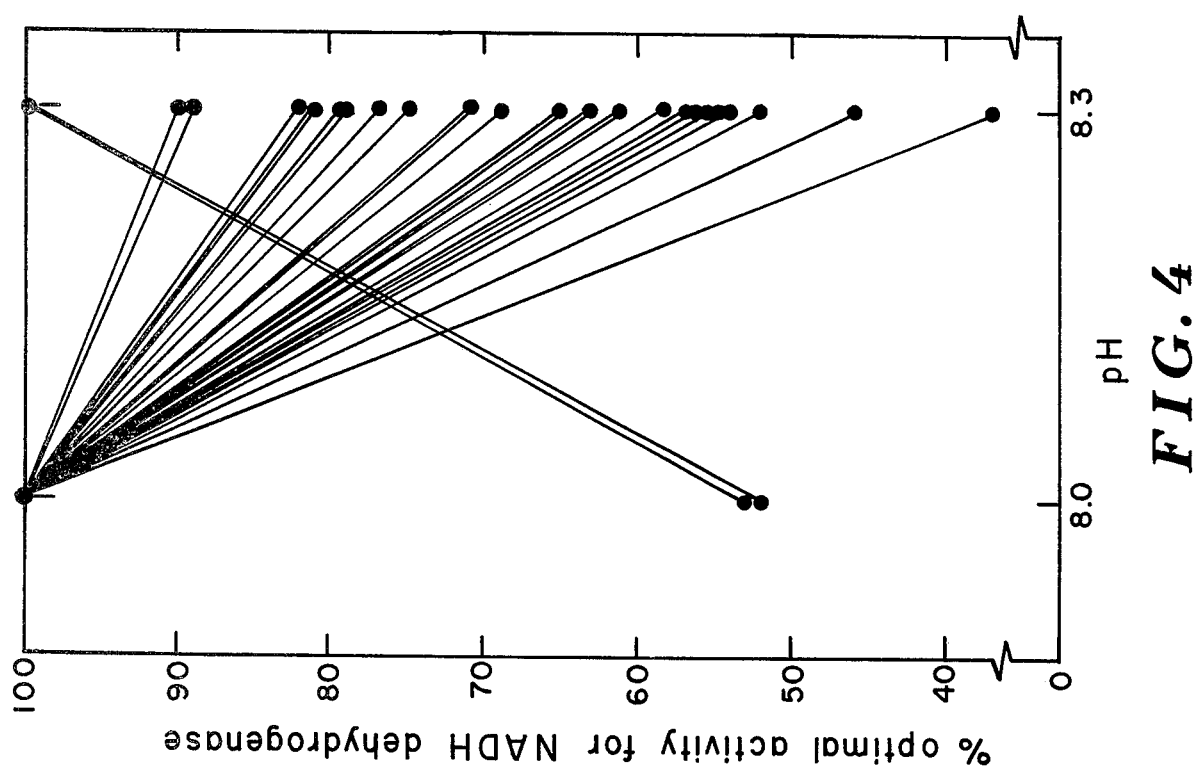
FIG. 4 shows graphically the results of carrier detection by assay of enzyme activity in lymphocyte cells from a random sample of thirty-one individuals.

The results of experiments involving a random sample of thirty-one individuals are illustrated in FIG. 4. Each line represents a different individual. Based on pH optima, twenty-nine of thirty-one individuals are non-carriers. Two of thirty-one (6 percent) are considered carriers for CF based on the assay. The theoretical carrier frequency is 5 percent.

EXAMPLES 5 AND 6

Assays of $O_2$ Consumption and Rotenone Inhibition

Confluent monolayers of fibroblasts as prepared in Example 1 were harvested by trypsin-EDTA digestion. Cells were pelleted by centrifugation at 600×g for 5 min, washed with 10 ml of cold Hank's Balanced Salt Solution (HBSS) containing 0.1 mg/ml bovine serum albumin and 10 mg/ml dextrose, pH 7.4. 100 µl aliquots of the washed cell suspension were taken for cell counting using a ZBI Coulter Counter. The washed cells were again pelleted by centrifugation and resuspended in 1 ml cold HBSS. $O_2$ consumption was measured polarographically on a cell suspension of $1 \times 10^7$ cells in a final volume of 3 ml by an $O_2$ electrode system (Clark model 53, Yellow Springs Instruments, Ohio). In additional experiments, rotenone (Sigma, St. Louis, Mo.) was used to specifically inhibit site 1 of the electron transport system. In these experiments the baseline $O_2$ uptake rate was determined for each cell line. Prior to removing the cells from the electrode chamber, 100 µl of 100 µM rotenone were added and $O_2$ consumption recorded. Preliminary experiments included the addition of 100 µl of 0.1 percent KCN to assess the extent of inhibition caused by this mitochondrial electron transport inhibitor. KCN completely abolished measurable $O_2$ uptake in all cell lines tested. $O_2$ uptake (n atoms $O_2$/min/$10^8$ cells) was greater in fibroblasts from CF subjects (N=6): 328.7±28.2 than in their controls (N=6): 199.5±22.8 and in those from heterozygote subjects (N=8): 227.7±17.7 than in their controls (N=8): 156.3±15.6 (P<0.005 by Student's t-test in both comparisons).

Figure 5:
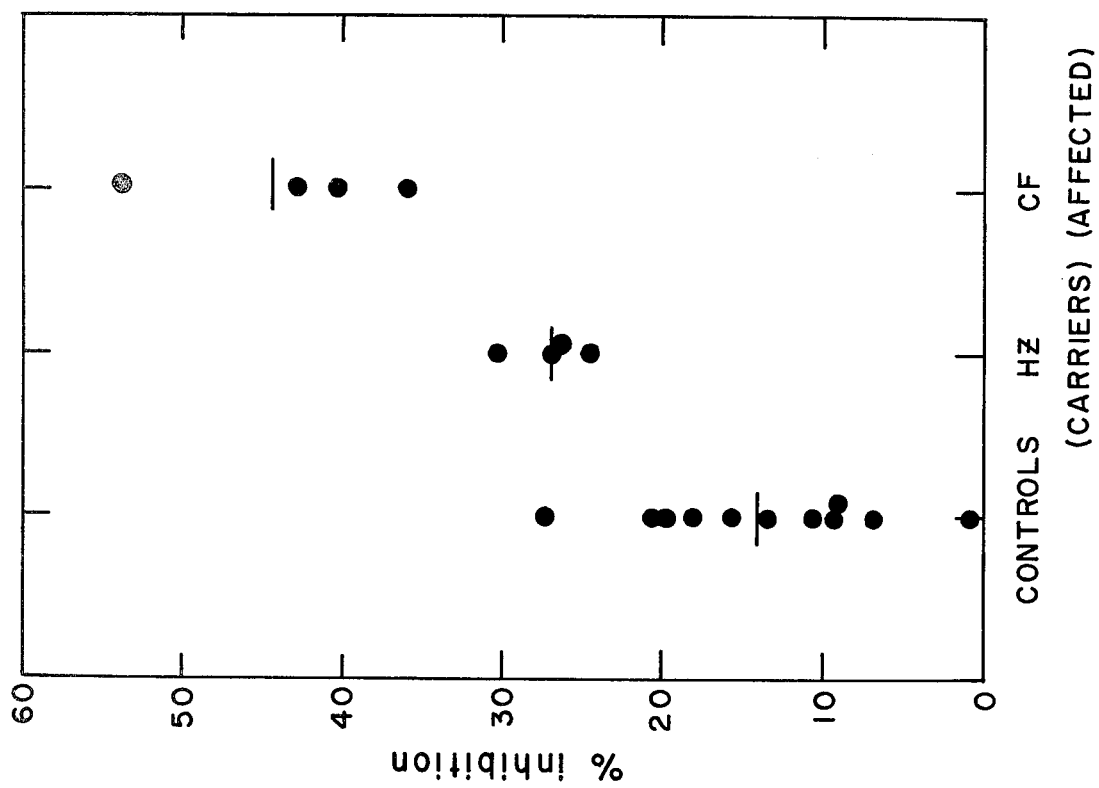
FIG. 5 shows graphically the inhibitory effect of rotenone on oxygen consumption by fibroblast cells from cystic fibrosis patients, carriers and controls.

At the dosage used, rotenone inhibited $O_2$ consumption in all cell strains tested but the inhibitory effect was CF>HZ>controls. The inhibitory effect of rotenone on $O_2$ consumption in the three genotypes is shown in FIG. 5. The change in $O_2$ consumption rate caused by rotenone was recorded as percent of initial $O_2$ consumption rate. Each point represents percent inhibition measured on one cell strain.

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. A method for the diagnosis of cystic fibrosis, the detection of non-symptomatic carriers of the disease and the identification of non-affected persons, which method comprises:
    (A) obtaining a sample of cells possessing mitochondria from a human subject,
    (B) preparing a homogenate of the cells,
    (C) performing an assay on the homogenate of cells which measures the mitochondrial activity of the cells, and
    (D) evaluating the assay by comparing the measurements with standards established as a result of similar assays of other subjects of known cystic fibrosis condition.

2. A method according to claim 1 wherein said assay is a kinetic assay of the enzyme complex of an energy conserving site of the mitochondrial electron transport system of the cells.

3. A method according to claim 2 wherein said enzyme is the enzyme of the first energy conserving site, NADH dehydrogenase.

4. A method according to claim 2 wherein said assay is a determination of the affinity of the enzyme for its substrate.

5. A method according to claim 4 wherein enzyme affinity for its substrate is measured at at least two of three pH values representing least alkaline conditions, more alkaline conditions and most alkaline conditions.

6. A method according to claim 5 further characterized in that said pH values are about 8.0, 8.3 and 8.6.

7. A method according to claim 2 wherein said assay is a determination of pH optimum for enzyme activity.

8. A method according to claim 7 wherein enzyme activity is measured at at least two of three pH values representing least alkaline conditions, more alkaline conditions and most alkaline conditions.

9. A method according to claim 8 wherein said pH values are about 8.0, 8.3 and 8.6.

10. A method for the diagnosis of cystic fibrosis, the detection of non-symptomatic carriers of the disease and identification of non-affected normal individuals, which method comprises:
    (A) obtaining a sample of venous blood from a human subject,
    (B) isolating the lymphocytes from said blood sample,
    (C) preparing a homogenate of the lymphocyte cells,
    (D) performing a kinetic assay of the NADH dehydrogenase enzyme complex of the first energy conserving site of the mitochondrial electron transport system of the lymphocyte cells by determination of the pH optimum for activity of said enzyme at pH values of about 8.0, 8.3 and 8.6, and
    (E) evaluating the assay by comparison with standards established as the result of similar assays of other subjects of known conditions.

11. A method according to claim 2 wherein said assay is a determination of temperature optimum for enzyme activity.

12. A method according to claim 2 wherein said assay is a determination of differential inhibition of enzyme activity.

13. A method according to claim 2 wherein said assay is a determination of differential electrophoretic mobility of the enzyme.

14. A method according to claim 1 wherein said asay is an assay of mitochondrial activity governed by the enzyme complex of an energy conserving site of the mitochondrial electron transport system of the cells.

15. A method according to claim 14 wherein said assay is a determination of calcium uptake by the mitochondria.

16. A method according to claim 14 wherein said assay is a determination of oxygen consumption by the mitochondria.

17. A method according to claim 14 wherein said assay is a determination of inhibition of oxygen consumption by the mitochondria.

* * * * *